United States Patent [19]

Dye et al.

[11] 4,029,087

[45] June 14, 1977

[54] EXTREMITY COMPRESSION DEVICE

[75] Inventors: John F. Dye, Reedsburg, Wis.; Charles R. Memhardt, Morton Grove, Ill.

[73] Assignee: The Kendall Company, Boston, Mass.

[22] Filed: Oct. 28, 1975

[21] Appl. No.: 625,967

[52] U.S. Cl. .......................................... 128/24 R
[51] Int. Cl.² ...................................... A61H 1/00
[58] Field of Search ......... 128/24 R, 64, 60, 38–40, 128/297, 299, DIG. 20

[56] References Cited

UNITED STATES PATENTS

| 1,608,239 | 11/1926 | Rosett | 128/24 R |
|---|---|---|---|
| 2,361,242 | 10/1944 | Rosett | 128/24 R |
| 2,528,843 | 11/1950 | Poor | 128/24 R |
| 2,533,504 | 12/1950 | Poor | 128/24 R |
| 2,781,041 | 2/1957 | Weinberg | 128/60 |
| 2,823,668 | 2/1958 | Van Court et al. | 128/DIG. 20 |
| 3,177,866 | 4/1965 | Wesslund | 128/24 R |
| 3,332,415 | 7/1967 | Ericson | 128/DIG. 20 |
| 3,454,010 | 7/1969 | Lilligren et al. | 128/24 R |
| 3,536,063 | 10/1970 | Werding | 128/24 R |
| 3,548,809 | 12/1970 | Conti | 128/64 X |
| 3,862,629 | 1/1975 | Rotta | 128/24 R |
| 3,885,554 | 5/1975 | Rockwell | 128/64 X |
| 3,901,225 | 8/1975 | Sconce | 128/24 R |

Primary Examiner—Lawrence W. Trapp
Attorney, Agent, or Firm—Powell L. Sprunger

[57] ABSTRACT

A device for applying compressive pressures against a patient's limb from a source of pressurized fluid comprising, an elongated pressure sleeve for enclosing a length of the patient's limb. The sleeve has a plurality of separate fluid pressure chambers progressively arranged longitudinally along the sleeve from a lower portion of the limb to an upper portion of the limb proximal the patient's heart relative the lower portion. The device has means for filling the chambers from the source during periodic compression cycles while applying a greater pressure in each lower chamber than the pressure in any upper chamber to apply a compressive pressure gradient against the patient's limb by the sleeve which progressively decreases from the lower to upper limb portions. The device also has means for emptying the chambers during periodic decompression cycles between the compression cycles.

27 Claims, 12 Drawing Figures

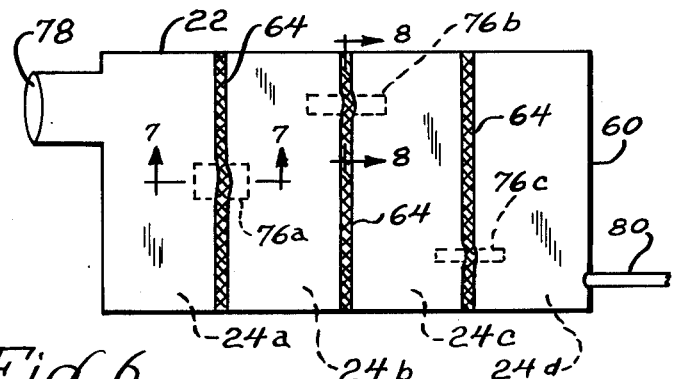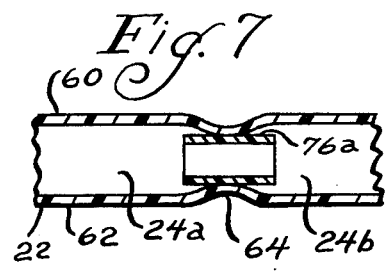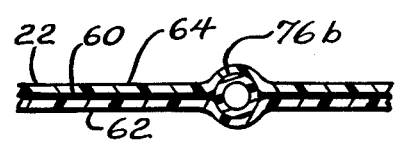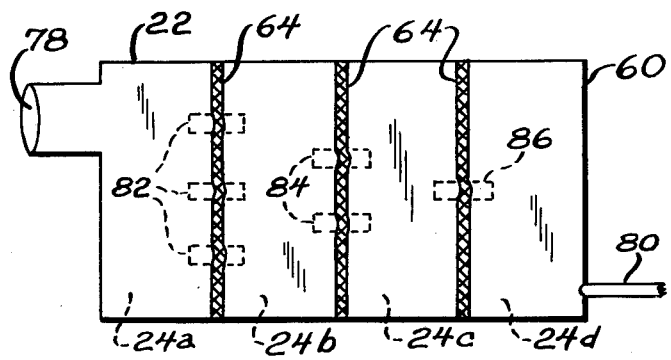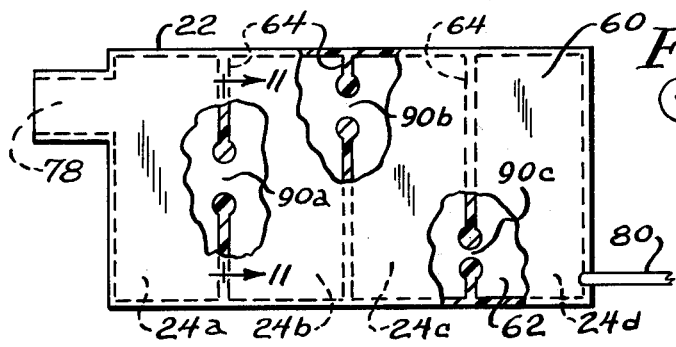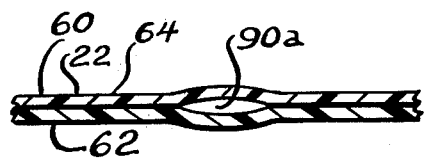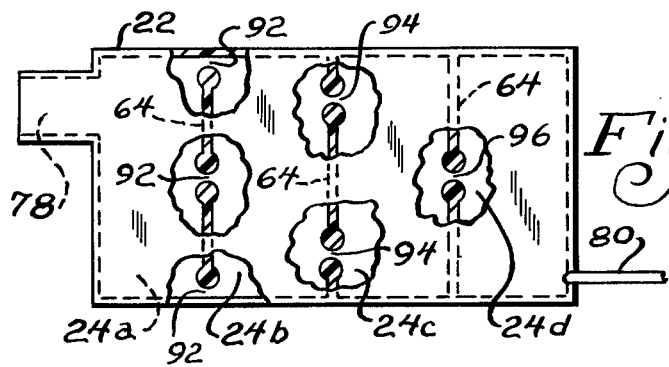

EXTREMITY COMPRESSION DEVICE

BACKGROUND OF THE INVENTION

The present invention relates to therapeutic and prophylactic devices, and more particularly to devices for applying compressive pressures against a patient's limb.

It is known that the velocity of blood flow in a patient's extremities, particularly the legs, markedly decreases during confinement of the patient. Such pooling or stasis of blood is particularly pronounced during surgery, immediately after surgery, and when the patient has been confined to bed for extended periods of time. It is also known that stasis of blood is a significant cause leading to the formation of thrombi in the patient's extremities, which may have a severe deleterious effect on the patient, including death. Additionally, in certain patients it is desirable to move fluid out of interstitial spaces in extremity tissues, in order to reduce swelling associated with edema in the extremities.

SUMMARY OF THE INVENTION

A principal feature of the present invention is the provision of a device of simplified construction for applying compressive pressures against a patient's limb in an improved manner.

The device of the present invention comprises an elongated pressure sleeve for enclosing a length of the patient's limb. The sleeve has a plurality of separate fluid pressure chambers progressively arranged longitudinally along the sleeve from a lower portion of the limb to an upper portion of the limb proximal the patient's heart relative the lower portion. The device has means for filling the chambers from a source of pressurized fluid during periodic compression cycles, and means for emptying the chambers during periodic decompression cycles between the compression cycles.

A feature of the present invention is that the filling means applies a greater pressure in each of the lower chambers than the pressure in any upper chamber.

Another feature of the present invention is that the device applies a compressive pressure gradient against the patient's limb by the sleeve which progressively decreases from the lower to upper portions of the limb.

Still another feature of the present invention is that the applied compressive pressure gradient enhances the flow of blood from the patient's extremity toward the heart.

Thus, a feature of the present invention is that the device deters formation of thrombi in the veins of the patient's extremity, and may be utilized to reduce edema in the extremity.

Another feature of the invention is that in an embodiment the device sequentially fills the compression chambers.

Yet another feature of the invention is that in another embodiment the device simultaneously fills the compression chambers.

A feature of the invention is that in an embodiment the device simultaneously empties the chambers.

Another feature of the invention is that in an embodiment the device sequentially empties the chambers.

Still another feature of the invention is the provision of means for controlling the duration of the periodic compression cycles.

Yet another feature of the invention is the provision of means for controlling the duration of the periodic decompression cycles.

Further features will become more fully apparent in the following description of the embodiment of this invention and from the appended claims.

DESCRIPTION OF THE DRAWINGS

In the drawings:

FIG. 6 is a plan view of another embodiment of a compression sleeve for the device of the present invention;

FIG. 7 is a fragmentary sectional view taken substantially as indicated along the line 7—7 of FIG. 6;

FIG. 8 is a fragmentary sectional view taken substantially as indicated along the line 8—8 of FIG. 6;

FIG. 9 is a plan view of another embodiment of a compression sleeve for the device of the present invention;

FIG. 10 is a plan view, partly broken away, illustrating another embodiment of a compression sleeve for the device of the present invention;

FIG. 11 is a fragmentary sectional view taken substantially as indicated along the line 11—11 of FIG. 10; and FIG. 12 is a plan view, partly broken away, of another embodiment of a compression sleeve for the device of the present invention.

DESCRIPTION OF THE PREFERRED EMBODIMENTS

Figure 1:
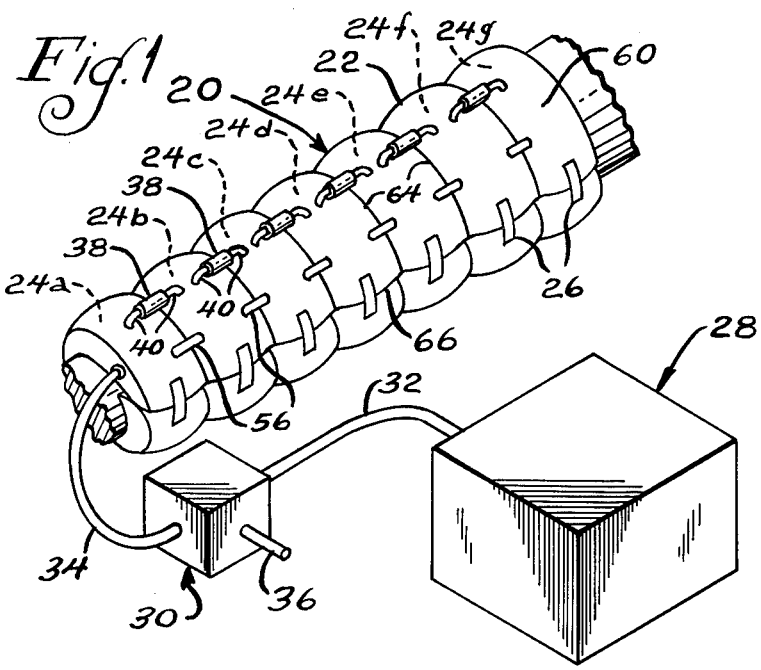
FIG. 1 is a perspective view of a compression applying device of the present invention showing a sleeve in the device secured about a patient's lower extremity.

Referring now to FIG. 1, there is shown a device generally designated 20 for applying compressive pressures against a patient's extremity of limb, such as the leg. The device has an elongated compression or pressure sleeve 22, which is shown in an inflated configuration, for enclosing a length of the patient's limb. For example, the sleeve 22 may extend from a lower region of the ankle to an upper region of the leg below the knee or above the knee, as desired. The sleeve 22 may be constructed from a sheet of flexible fluid impervious material, as will be described below.

Figure 2:
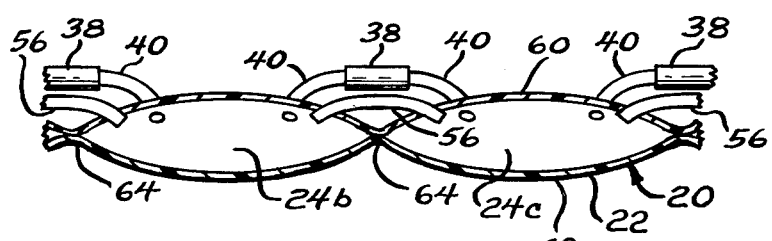
FIG. 2 is a fragmentary sectional view of the sleeve in the device of FIG. 1.

As illustrated in FIGS. 1 and 2, the sleeve 22 has a plurality of separate fluid pressure chambers 24a, 24b, 24c, 24d, 24e, 24f, and 24g which extend laterally in the sleeve 22, and which are progressively disposed longitudinally along the sleeve 22 from a lower to an upper portion of the patient's limb. The sleeve 22 may be wrapped around the patient's leg, and may be releasably secured about the limb by any suitable fastening means, such as fastening strips or tapes 26, as shown.

The compression device 20 has a timing device 30 which is connected through a conduit 32 to a source 28 of pressurized gas, such as a compressor for generating the source. The timing device 30 is connected through a conduit 34 to a lowermost chamber 24a in the sleeve, and to an exhaust tube 36 for deflating the sleeve 22. The source 28 of pressurized gas is continuously supplied to the timing device 30, while the timing device 30 connects the chamber 24a at periodic intervals through the conduit 34 to the source 28. At other periodic intervals, the timing device 30 connects the conduit 34 and chamber 24a to the exhaust tube 36. Thus the timing device 30 connects the source 28 of pressurized gas to the lowermost chamber 24a during periodic inflation or compression cycles when the sleeve is filled, and the timing device 30 connects the inflated lowermost chamber 24a of the sleeve 22 to the exhaust tube 36 during periodic deflation or decompression cycles, i.e., the interval between the inflation cycles, when the sleeve is emptied. In this manner, the sleeve 22 is sequentially inflated and deflated, with the duration of the compression and decompression cycles being adjustable by suitable adjustment of the timing device 30.

Figure 3:
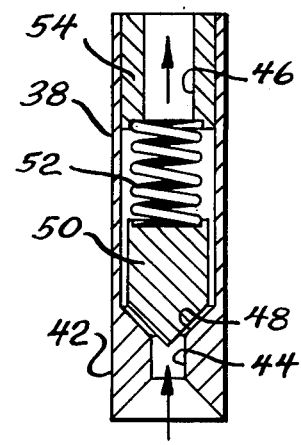
FIG. 3 is a sectional view of valve means for the sleeve in the device of FIG. 1.

As illustrated in FIGS. 1–3, the sleeve 22 has a plurality of spring valves 38 connected between adjoining chambers of the sleeve by associated pairs of tube sections 40. As shown in FIG. 3, the spring valves 38 have a valve housing 42 defining inlet and outlet ports 44 and 46 which respectively communicate through the tube sections 40 with lower and upper chambers of adjoining chambers in the sleeve. The valve housing 42 has an annular seat 48 surrounding the inlet port 44, and a plug or valve member 50 is slidably retained in the housing 42 for sealingly engaging against the seat 48. The valve member 50 is biased against the seat 48 by a helical spring 52 which extends between a retaining member 54 in the housing and an inner end of the valve member 50, as shown.

The spring valves 38 prevent passage of gas from the inlet port 44 to the outlet port 46 so long as the spring 52 retains the plug member 50 in sealing engagement against the seat 48. Referring to FIGS. 1–3, it will be recalled that the lowermost chamber 24a is connected to the source 28 of pressurized gas by the timing device 30 during each compression cycle, and, accordingly, the lowermost chamber 24a is the first chamber in the sleeve which undergoes inflation. Since the lowermost spring valve 38 initially prevents passage of air from the lowermost chamber 24a to the adjoining upper chamber 24b, the adjoining chamber 24b is not inflated until the pressure in the lowermost chamber 24a exceeds the pressure in the upper adjoining chamber 24b by a predetermined amount, as determined by the strength characteristics in the spring 52 of this valve. As the lowermost chamber 24a is inflated, the pressure in the lowermost chamber 24a increases until predetermined pressure difference between the adjoining chambers has been exceeded, at which time the relative pressure differential in the adjoining chambers causes the valve member 50 to move away from the seat 48, thus permitting passage of gas from the lowermost chamber 24a through the spring valve 38 to the adjoining chamber 24b, resulting in inflation of the chamber 24b. Accordingly, the adjoining upper chamber 24b is not inflated until the pressure in the lower chamber 24a exceeds the pressure in the upper chamber 24b by the predetermined amount.

Once the spring valve 38 between the chambers 24a and 24b has opened, the valve serves to maintain the pressure difference in these two chambers above the predetermined amount during further inflation of the lowermost chamber 24a, since the valve between the chambers will temporarily close if this condition is not satisfied. In this manner, the device initially inflates the lowermost chamber 24a, and then simultaneously inflates the two lower chambers 24a and 24b while maintaining the predetermined pressure difference between the chambers. When the pressure in the second chamber 24b exceeds the pressure in the adjoining upper chamber 24c by a predetermined amount, as determined by the spring valve between the chambers, the spring valve opens, in a manner as previously described, and permits passage of gas from the chamber 24b to the upper adjoining chamber 24c in the sleeve. During inflation of the chamber 24c, the two lower spring valves cause simultaneous inflation of the lower chambers 24a, 24b, and 24c, while maintaining the predetermined pressure differences between the adjoining chambers 24a and 24b and between the adjoining chambers 24b and 24c. The remaining upper chambers 24d, e, f, and g in the sleeve 22 are inflated in a similar manner. Thus, the device 20 sequentially initiates inflation of the chambers from a lower to an upper part of the sleeve. After inflation of a given set of lower chambers has been initiated, the device simultaneously inflates the set of chambers while maintaining the pressure differences between chambers in the set of chambers.

It will thus be apparent that during each compression cycle, the pressure in each lower chamber will be greater than the pressure in any upper chamber, such that the pressures in the various chambers reduce from a lower to an upper part of the sleeve throughout the compression cycle. Accordingly, the sleeve 22 applies a compressive pressure gradient against the patient's leg which decreases from a lower to upper part of the sleeve, and thus increases the velocity of blood flow through the patient's leg in an upward direction toward the patient's heart, in order to reduce pooling of blood in the leg and deter formation of thrombi in the legs.

Figure 4:
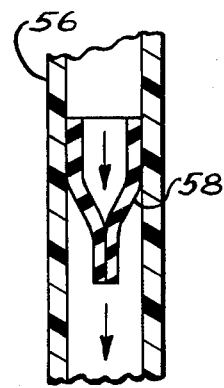
FIG. 4 is a fragmentary sectional view of valve means for the sleeve in the device of FIG. 1.

When all the chambers of the sleeve 22 have been inflated and the compression cycle has been completed, the timing device 30 connects the conduit 34 to the exhaust tube 36 in order to initiate the deflation or decompression cycle. As illustrated in FIGS. 1, 2, and 4, the sleeve 22 has a plurality of deflation tubes 56 connected between adjoining chambers in the sleeve. As shown in FIG. 4, a one-way flap valve 58 is secured in each of the deflation tubes 56. The valves 58 are arranged to prevent the passage of air from a lower chamber through the tubes 56 to an adjoining upper chamber, and thus prevent passage of air through the tubes 56 during the inflation cycles of the sleeve. However, the valves 58 permit passage of air through the tubes 56 from an upper chamber to a lower adjoining chamber when the pressure in the lower adjoining chamber is less than the pressure in the upper adjoining chamber.

Thus, referring to FIGS. 1 and 2, the lowermost chamber 24a is deflated or emptied through the conduit 34 and exhaust tube 36 during each deflation cycle until the pressure in the lowermost chamber 24a is slightly less than the pressure in the adjoining upper chamber 24b at which time air passes from the chamber 24b into the chamber 24a through the lower deflation tube 56 and associated valve 58 and from the chamber 24a through the exhaust tube 36 to the atmosphere. Consequently, both chambers 24a and 24b are simultaneously deflated while the pressure in the lowermost chamber 24a remains slightly less than the pressure in the chamber 24b. When the pressure in the partially deflated chamber 24b becomes slightly less than the pressure in the inflated chamber 24c, air begins to pass from the chamber 24c through the associated tube 56 and valve 58 into the adjoining lower chamber 24b, after which the air passes into the chamber 24a and through the conduit 34 and exhaust tube 36 to the atmosphere. The upper chamber 24d, c, e, f, and g are deflated in a similar manner through the various deflation tubes 56 and associated valves 58. Thus, the device 20 sequentially initiates deflation of the chambers during the deflation cycles. After the sleeve 22 has been deflated through the exhaust tube 36, the timing device 30 undergoes a delay during the deflation or decompression cycle before again connecting the air source 28 to the lowermost chamber 24a at the start of the next compression cycle. Accordingly, the sleeve periodically applies a compressive pressure gradient against the patient's limb during the compression cycles, and periodically removes the compressive pressure from the patient's limb during the decompression cycles between the compression cycles.

Referring to FIGS. 1 and 2, the sleeve 22 may comprise a pair of sheet segments 60 and 62 of a flexible fluid impervious sheet, such as polyvinyl chloride. The segments 60 and 62 may be secured together along laterally extending line 64, such as by heat sealing, to define the separate contiguous chambers. If desired, the segments 60 and 62 may be formed by folding a single sheet along a fold line 66 adjacent an edge of the sleeve, as illustrated in FIG. 1, or separate pieces may be used as the segments 60 and 62 to make the sleeve.

Figure 5:
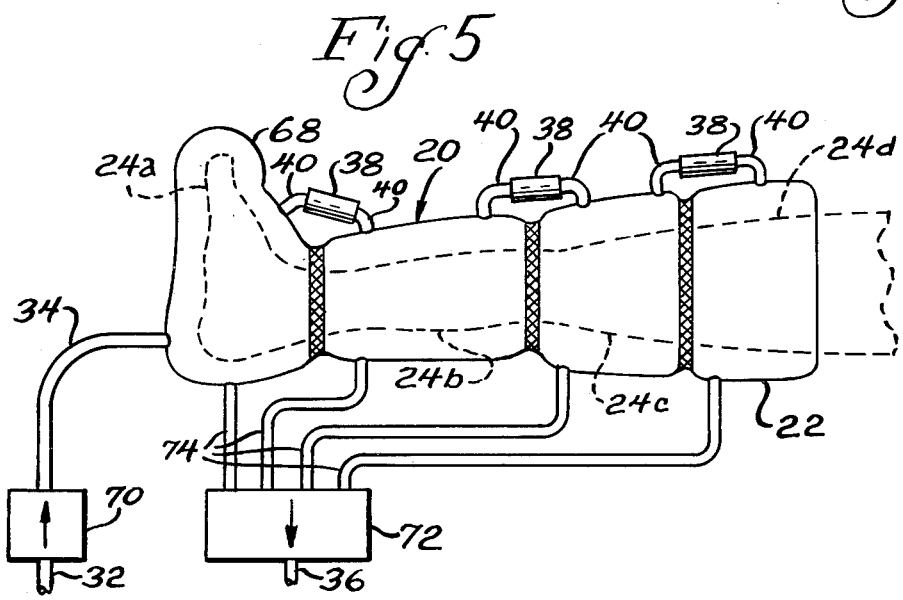
FIG. 5 is an elevational view of another embodiment of the compression applying device of the present invention.

Another embodiment of the compression applying device 20 of the present invention is illustrated in FIG. 5, in which like reference numerals designate like parts. In this embodiment, the sleeve 22 has a foot portion 68 defining the lowermost chamber 24a for enclosing and compressing the patient's foot. As before, the sleeve 22 has a plurality of tube sections 40 and associated spring valves 38 connecting adjoining chambers for inflation of the various chambers during the compression cycles, as controlled by a timing device 70 connected between an inflation conduit 34 and a conduit 32 from the air source. However, in this embodiment, each of the chambes is separately connected to an exhaust timer 72 through conduits 74, such that the timer 72 simultaneously connects the conduits 74 to the exhaust tube 36 in order to simultaneously deflate all of the chambers in the sleeve 22. Accordingly, the sleeve 22 is inflated through the conduit 34 by the source of pressurized gas during the compression cycles, in a manner as previously described. After each of the compression cycles has been completed, all of the sleeve chambers are simultaneously deflated by the timer 72 through the exhaust tube 36 to the atmosphere.

Another embodiment of the sleeve 22 of the present invention is illustrated in FIGS. 6-8, in which like reference numerals designate like parts. The sleeve 22 has a plurality of chambers 24a-24d defined by laterally extending lines 64 connecting segments 60 and 62 of a sheet material, as previously described. In this embodiment, the sleeve 22 has a plurality of tube sections 76a, 76b, and 76c positioned intermediate the sheet segments 60 and 62, and separately connecting adjoining chambers. Thus, the tube sections 76a communicates between the lower adjoining chambers 24a and 24b, the tube section 76b communicates between the adjoining chambers 24b and 24c, and the tube section 76c communicates between the adjoining chambers 24c and 24d. The tube sections 76a, b, and c have lumens of successively decreasing diameter to provide a port or opening between adjoining chambers of progressively decreasing effective size between progressively located upper adjoining chambers.

Accordingly, the large port 78 communicating with the lowermost chamber 24a permits free passage of gas to the lowermost chamber 24a, while the tube section 76a slightly impedes or limits passage of gas from the lowermost chamber 24a into the upper adjoining chamber 24b. Similarly, the tube section 76b, which has a lumen of reduced size relative the tube section 76a, further impedes passage of gas from the chamber 24b into the upper adjoining chamber 24c. Finally, the most narrow tube section 76c further impedes passage of gas from the chamber 24c into the uppermost chamber 24d. Although the various chambers in the sleeve of FIGS. 6-8 are simultaneously inflated, the sleeve applies a pressure gradient against the patient's limb which decreases from the lower chamber 24a to the upper chamber 24d during the compression cycles. This follows since the lowermost chamber 24a freely inflates, while the tube section 76a limits passage of air somewhat from the chamber 24a into the chamber 24b, such that a higher pressure is maintained in the chamber 24a than in the chamber 24b during the compression cycle. Similarly, the thinner tube section 76b restricts passage of gas from chamber 24b into 24c to a greater extent than through the tube section 76a, and thus maintains a higher pressure in the chamber 24b than in chamber 24c during the compression cycle. Finally, the smallest tube section 76c further limits passage of air into the uppermost chamber 24d, and maintains a higher pressure in chamber 24c than in chamber 24d during the compression cycles. In this manner, during the compression cycles the pressure in the chamber 24a will be greater than the pressure in chamber 24b, the pressure in chamber 24b will be greater than the pressure in chamber 24c, and the pressure in chamber 24c will be greater than than in chamber 24d. Accordingly, the sleeve applies a compressive pressure gradient against the patient's leg which decreases from a lower part of the sleeve toward an upper part of the sleeve. The sleeve 22 may be deflated through an exhaust tube 80 connected to the uppermost chamber 24d, or in a manner as previously described.

Another embodiment of the sleeve 22 of the present invention is illustrated in FIG. 9, in which like reference numerals designate like parts. In this embodiment, the sleeve has three tube sections 82 which have lumens of approximately equal size and which communicate between the lowermost chamber 24a and the upper adjoining chamber 24b. The sleeve 22 also has a pair of tube sections 84 which have lumens of approximately equal size and which communicate between the adjoining chambers 24b and 24i c. Also, the sleeve has a single tube section 86 which has a lumen of a size approximately equal to the size of the lumens in the tube sections 82 and 84, and which communicate between the chamber 24c and the uppermost chamber 24d. Thus, the effective size of the openings between the chambers 24a and 24b is greater than the effective size of the openings between the chambers 24b and 24c, while the effective size of the openings between the chambers 24b and 24c is greater than the effective size of the opening between the chambers 24c and 24d. Accordingly, the sleeve 22 of FIG. 9 operates in a manner similar to that described in connection with the sleeve of FIGS. 6-8 in order to develop a compression pressure gradient against the patient's limb during the periodic compression cycles.

Another embodiment of the sleeve 22 of the present invention is illustrated in FIGS. 10 and 11, in which like reference numerals designate like parts. In this embodiment, the connecting or seal lines 64 in the sleeve 22 are interrupted to define openings 90a, 90b, and 90c which communicate between adjoining chambers. As shown, the opening 90a communicates between the chambers 24a and 24b, the opening 90b communicates between the chambers 24b and 24c, while the opening 90c communicates between the chambers 24c and 24d. Also, the size of the opening 90a is greater than the size of the opening 90b, while the size of the opening 90b is greater than the size of the opening 90c. Accordingly, the sleeve 22 has openings which progressively decrease in size between progressively located upper chambers in the sleeve, in a configuration similar to that described in connection with FIGS. 6–8, such that the sleeve 22 of FIGS. 10 and 11 also applies a compressive pressure gradient against the patient's leg during the periodic inflation cycles.

Another embodidment of the sleeve 22 of the present invention is illustrated in FIG. 12, in which like reference numerals designate like parts. In this embodiment, the various connecting or seal line 64 are interrupted to define openings between adjoining chambers which have approximately an equal size. However, the sleeve 22 has three openings 92 of approximately equal size communicating between the lowermost chamber 24a and the adjoining upper chamber 24b, the sleeve has a pair of openings 94 communicating between the chamber 24b and the adjoining upper chamber 24c, while the sleeve has a single opening 96 of approximately the same size communicating between the chamber 24c and the uppermost chamber 24d. Thus, the effective size of the openings progressively decreases between progressively located upper adjoining chambers, and the sleeve 22 of FIG. 12 operates in a manner similar to that described in connection with the sleeves of FIGS. 6–11 to apply a compressive pressure gradient against the patient's leg.

The foregoing detailed description is given for clearness of understanding only, and no unnecessary limitations should be understood therefrom, as modifications will be obvious to those skilled in the art.

We claim:

1. A device for applying compressive pressures against a patient's limb from a source of pressurized fluid comprising:
    an elongated pressure sleeve for enclosing a length of the patient's limb, said sleeve having a plurality of separate fluid pressure chambers progressively arranged longitudinally along the sleeve from a lower portion of the limb to an upper portion of the limb proximal the patient's heart relative said lower portion;
    means for filling said chambers from said source during periodic compression cycles while applying a greater pressure in each inflated lower chamber than the pressure in any upper inflated chamber to apply a compressive pressure gradient against the patient's limb by the sleeve which progressively decreases from said lower to upper limb portions throughout the compression cycles, said filling means including means for connecting the source to a lower first chamber in said sleeve;
    means for distributing fluid from said first chamber to progressively located upper chambers at progressively decreasing pressures; and
    means for emptying said chambers during periodic decompression cycles between said compression cycles.

2. The device of claim 1 wherein the distributing means comprises, means for connecting each lower chamber to an adjoining upper chamber, and means for limiting passage of fluid from the lower to upper adjoining chambers.

3. The device of claim 2 wherein the limiting means comprises valve means for preventing passage of fluid through the connecting means responsive to a pressure difference between adjoining chambers less than a predetermined amount, and for permitting passage of fluid from the lower to upper adjoining chambers responsive to a pressure difference between said adjoining chambers greater than said predetermined amount.

4. The device of claim 3 wherein the valve means comprises, a valve housing having inlet and outlet ports respectively communicating between adjoining lower and upper chambers, a valve seat adjacent said inlet port, a valve member retained in the housing for movement toward and away from said seat, and means for biasing said valve member in sealing engagement against said seat for preventing passage of fluid from said inlet port to said outlet port, said biasing means permitting movement of said valve member away from said seat responsive to a pressure in said inlet port greater than the pressure in said outlet port by a predetermined amount to permit passage of fluid from said inlet port to said outlet port.

5. The device of claim 1 wherein the distributing means comprises means for connecting adjoining chambers, the connecting means defining opening means of progressively decreasing effective size between progressively located upper chambers.

6. The device of claim 5 wherein the connecting means comprises a plurality of conduit sections communicating between adjoining chambers.

7. The device of claim 6 wherein said sleeve comprises a pair of flexible fluid impervious sheets being connected together to define said chambers, with said conduit sections being located intermediate said sheets.

8. The device of claim 5 wherein said sleeve comprises a pair of flexible fluid impervious sheets, said sheets being connected together along a plurality of laterally extending lines to define said chambers, said lines being interrupted to define said opening means communicating between adjoining chambers.

9. The device of claim 5 wherein the connecting means defines a single opening communicating between each adjoining chamber.

10. The device of claim 5 wherein the connecting means defines a progressively decreasing number of approximately equal sized openings communicating between progressively located upper adjoining chambers.

11. The device of claim 1 wherein said filling means sequentially fills said chambers.

12. The device of claim 1 wherein said filling means simultaneously fills said chambers.

13. The device of claim 1 wherein said sleeve encloses a portion of the patient's leg, and in which said sleeve includes a foot portion defining a lower chamber for extending around the patient's foot.

14. The device of claim 1 wherein said emptying means simultaneously empties said chambers.

15. The device of claim 1 wherein said emptying means sequentially empties said chambers.

16. The device of claim 1 including fluid exhaust means, and conduit means separately connecting each of said chambers to said exhaust means.

17. The device of claim 1 including fluid exhaust means, and means for connecting said exhaust means to a lower first chamber in said sleeve.

18. The device of claim 17 including means for connecting adjoining chambers for passages of fluid from upper chambers to said first lower chamber.

19. The device of claim 1 including timing means for controlling the duration of said compression cycles.

20. The device of claim 1 including timing means for controlling the duration of said decompression cycles.

21. A sleeve for applying compressive pressures against a patient's limb, comprising:
 a pair of flexible fluid impervious sheets;
 means for securing said sheets together and defining a plurality of laterally extending fluid chambers disposed longitudinally between lower and upper portions of the sleeve;
 means for releasably attaching said sleeve about the patient's limb with said chambers encircling a length of the limb; and
 valve means connecting each lower chamber to an adjoining upper chamber, said valve means preventing passage of fluid from the lower to upper adjoining chambers, and permitting passage of fluid from the upper to lower adjoining chambers responsive to a pressure in said lower adjoining chambers less than the pressure in said upper adjoining chambers.

22. The sleeve of claim 21 wherein the securing means comprises a plurality of seal lines connecting said sheets together.

23. The sleeve of claim 21 wherein said sheets are connected at one edge by a fold line.

24. A device for applying compressive pressures against a patient's limb from a source of pressurized fluid, comprising:
 an elongated pressure sleeve for enclosing a length of the patient's limb, said sleeve having a plurality of separate fluid pressure chambers progressively arranged longitudinally along the sleeve from a lower portion of the limb to an upper portion of the limb proximal the patient's heart relative said lower portion;
 means for sequentially initiating inflation of said chambers from said source through a lowermost chamber progressively from a lower to upper chamber in the sleeve during periodic inflation cycles, and for simultaneously inflating the initiated chambers during the inflation cycles while maintaining predetermined pressure difference between adjoining chambers and applying a compressive pressure gradient against the patient's limb which decreases upwardly along the sleeve; and
 means for deflating said chambers during periodic deflation cycles between said inflation cycles.

25. A device for applying compressive pressures against a patient's limb from a source of pressurized fluid, comprising:
 an elongated pressure sleeve for enclosing a length of the patient's limb, said sleeve having a plurality of separate fluid pressure chambers progressively arranged longitudinally along the sleeve from a lower portion of the limb to an upper portion of the limb proximal the patient's heart relative said lower portion, said sleeve comprising a pair of flexible fluid impervious sheets, means for connecting said sheets together defining said chambers extending laterally between said sheets, and means for releasably securing said sleeve about the patient's limb;
 means for filling said chambers from said source through a lowermost chamber during periodic compression cycles while applying a greater pressure in each inflated lower chamber than the pressure in any upper inflated chamber to apply a compressive pressure gradient against the patient's limb by the sleeve which progressively decreases from said lower to upper limb portions throughout the compression cycles; and
 means for emptying said chambers during periodic decompression cycles between said compression cycles.

26. A device for applying compressive pressures against a patient's limb from a source of pressurized fluid, comprising
 an elongated pressure sleeve for enclosing a length of the patient's limb, said sleeve having a plurality of separate fluid pressure chambers progressively arranged longitudinally along the sleeve from a lower portion of the limb to an upper portion of the limb proximal the patient's heart relative said lower portion, including one-way valve means connected between adjoining chambers, said valve means preventing passage of fluid from a lower chamber to an upper chamber in said adjoining chambers responsive to a pressure in said lower adjoining chamber greater than the pressure in said upper adjoining chamber, and permitting passage of fluid from said upper chamber to said lower chamber in said adjoining chambers responsive to a pressure in said lower adjoining chamber less than the pressure in said upper adjoining chamber;
 means for filling said chambers from said source during periodic compression cycles while applying a greater pressure in each lower chamber than the pressure in any upper chamber to apply a compressive pressure gradient against the patient's limb by the sleeve which progressively decreases from said lower to upper limb portions; and
 means for emptying said chambers during the periodic decompression cycles between said compression cycles, including fluid exhaust means, and means for connecting said exhaust means to a lower first chamber in said sleeve.

27. A sleeve for applying compressive pressures against a patient's limb, comprising:
 a pair of flexible fluid impervious sheets;
 means for securing said sheets together and defining a plurality of laterally extending fluid chambers disposed longitudinally between lower and upper portions of the sleeve;
 means for connecting adjoining chambers of the sleeve comprising, opening means of progressively decreasing effective size between progressively located upper chambers; and
 means for releasably attaching said sleeve about the patient's limb with said chambers encircling a length of the limb.

* * * * *